United States Patent [19]

Klostermann et al.

[11] Patent Number: 5,552,184
[45] Date of Patent: Sep. 3, 1996

[54] COATING AGENTS, THEIR USE AS CLEAR COATS AND PROCESSES FOR THE PRODUCTION OF MULTICOAT LACQUER FINISHES

[75] Inventors: Peter Klostermann; Hans-Martin Schönrock, both of Wuppertal; Klaus Schröter, Schwelm; Thomas Kutzner, Sprockhövel, all of Germany

[73] Assignee: Herberts GmbH, Wuppertal, Germany

[21] Appl. No.: 358,055

[22] Filed: Dec. 16, 1994

Related U.S. Application Data

[63] Continuation of Ser. No. 178,591, Jan. 7, 1994, abandoned, which is a continuation of Ser. No. 16,650, Feb. 12, 1993, abandoned.

[30] Foreign Application Priority Data

Feb. 15, 1992 [DE] Germany .......................... 42 04 611.4

[51] Int. Cl.⁶ ............................................. B05D 5/00
[52] U.S. Cl. ................. 427/284; 427/285; 427/385.5; 427/391; 427/393; 427/422; 528/230; 428/423.1
[58] Field of Search ............................ 427/284, 422, 427/285, 385.5, 391, 393; 528/230; 428/423.1

[56] References Cited

U.S. PATENT DOCUMENTS

| | | | |
|---|---|---|---|
| 4,419,407 | 12/1983 | Piccirilli | 428/423.1 |
| 4,812,523 | 3/1989 | Toman | 525/162 |
| 5,057,342 | 10/1991 | Hoy et al. | 427/422 |
| 5,219,616 | 6/1993 | Klostermann et al. | 427/284 |

FOREIGN PATENT DOCUMENTS

| | | |
|---|---|---|
| 0321607 | 12/1987 | European Pat. Off. . |
| 0452786 | 4/1991 | European Pat. Off. . |
| 2520372 | 7/1983 | France . |
| 2629930 | 2/1977 | Germany . |
| 3402827 | 8/1986 | Germany . |

*Primary Examiner*—Nathan M. Nutter
*Assistant Examiner*—Richard Jones
*Attorney, Agent, or Firm*—Keck, Mahin & Cate

[57] ABSTRACT

A coating agent with a viscosity of 100–1000 mPa.s, measured by rotational viscometry at 70° C. and a shear rate of 235 s$^{-1}$, containing 45–85 wt % of one or more polyesters, that have a branched structure and are essentially free from aromatic structural units, with a number-average molecular weight ($M_n$) of 350–3000 and a polydispersity of less than 3.5, 10–40 wt % of one or more cross-linkers based on aminoplastic resins and/or blocked di- and/or polyisocyanates, 0–20 wt % of one or more reactive diluents, and 0–10 wt % of one or more organic solvents.

They are particularly suitable as hot-sprayable clear coats for multicoat lacquer finishes.

11 Claims, No Drawings

5,552,184

COATING AGENTS, THEIR USE AS CLEAR COATS AND PROCESSES FOR THE PRODUCTION OF MULTICOAT LACQUER FINISHES

This is a continuation application of Ser. No. 08/178,591, filed on Jan. 7, 1994, now abandoned, which is a continuation of application Ser. No. 08/016,650. filed on Feb. 2, 1993, now abandoned, the text of which is hereby incorporated by reference.

FIELD OF THE INVENTION

The invention relates to coating agents based on polyester resins, aminoplastic resins and/or blocked di- and/or polyisocyanates that constitute a highly solids-rich one-component stoving system. They are particularly suitable for use as hot-sprayable clear coats for the production of multicoat lacquer finishes.

BACKGROUND OF THE INVENTION

Present-day automobile series lacquer finishes mostly consist of a clear coat/base coat finish that is applied to an electrophoretically primed and filler-coated bodywork. In the course of this, base coat and clear coat are preferably applied wet-on-wet, i.e. the base coat, after a flashing-off period, and optionally with heating and after subsequent application of a clear coat, is stoved together with the latter, as described e.g. in EP-A-0 038 127 and EP-A-0 402 772. Clear coatings suitable in this connection are described e.g. in EP-A-0 038 127 and EP-A-0 184 761.

In the case of the use both of one-component (1K) and of two-component (2K) clear coats, the lacquering operation is associated with emissions of environmentally harmful solvents. In the context of increasing efforts to protect the environment, the lacquer industry and the lacquer user take trouble that solvent emissions are largely avoided. A possibility is the use of 2-component systems. In the case for example of isocyanate-crosslinking 2-component clear coats, e.g. according to DE-OS 33 22 037 or DE-PS 36 00 425, overspray recycling is naturally not possible. As a result, that yields an increased amount of waste.

A further way of achieving this objective is the use of one-component highly solids-rich stoving clear coats in the production of multicoat lacquer finishes. However, the solvent content of such lacquer systems is generally at least 50 wt %. U.S. Pat. No. 4,419,407 even describes clear coats with a resin solids content of up to 65 wt % that can be used, applied wet-on-wet to flashed-off base coats, for the production of a multicoat lacquer finish. Those lacquers have the drawback that their application-technology properties as well as the surface of the finished coating are less advantageous than for lacquers with lower solids content.

DE-OS 22 53 300 describes hot-sprayable, solvent-free or low-solvent lacquer systems based on high-molecular polyesters with molecular weights of 1500 to 5000, low-molecular polyols and melamine resins. Alkyd resins in particular are described as polyesters. The examples still contain proportions of solvent of more than 20 % in the coating agents. These serve to reduce the viscosity.

DE-PS 26 29 930 describes hot-sprayable stoving coating agents, solvent-free or containing only low proportions of solvent, that are based on linear polyester resins with acid numbers below 15, preferably below 5 mg KOH/g, and methoxymelamine resin as crosslinker. The polyester resins contain aromatic structural units.

Pigmented coating agents are described both in DE-PS 22 53 300 and in DE-PS 26 29 930. Also these products are not sufficiently stable towards ultraviolet radiation.

SUMMARY OF THE INVENTION

It is the object of the present invention to make available liquid, one-component, highly solids-rich stoving lacquer system that is particularly suitable for clear coatings, is recyclable and enables the solvent emission to be kept low.

This problem is solved by making available a coating agent for a multicoat lacquer finish that contains 45–85 wt % of one or more polyester resins (I) as well as 10–40 wt % of at least one aminoplastic resin and/or blocked polyisocyanate as crosslinker (II), each relative to the whole coating agent, wherein (I) has a branched structure and is essentially free from aromatic structural units, has a number average molecular weight ($M_n$) of 350–3000 and a polydispersity of no more than 3.5, and a viscosity of 100–1000 mPa.s measured by rotational viscometry at 70° C. and a shear rate of 235 $s^{-1}$. The coating agent according to the invention can optionally also contain solvents, reactive diluents and further lacquer-technology additives. It can be applied hot, and it can optionally be brought into a form ready for application by injecting supercritical solvents.

DETAILED DESCRIPTION OF THE PREFERRED EMBODIMENTS

The polyester resins used according to the invention are of branched structure and contain essentially no aromatic structural units. They have a lower limit of the acid number of 12, preferably of 14 mg KOH/g; the upper limit of the acid number is 25, preferably 20 mg KOH/g; the lower limit of the hydroxyl number is 100, preferably 135, particularly preferably 180 mg KOH/g; the upper limit of the hydroxyl number is 300, preferably 275, particularly preferably 240 mg KOH/g. Depending on the choice of educts and the conduct of the reaction, the polyester resins to be used according to the invention have number-average molecular weights of 350 to 3000, preferably of 500 to 1500 or of 1000 to 2000. (Determination by gel permeation chromatogaphy with polystyrene standard). The polydispersity ($M_w/M_n$) of the polyester resins used according to the invention must not exceed a value of 3.5.

The polyester resins used according to the invention are produced by polycondensation of aliphatic and/or cycloaliphatic, optionally unsaturated, mono- and/or dicarboxylic acids, free from aromatic structural units, and/or their anhydrides with aliphatic and/or cycloaliphatic mono- und/or polyalcohols and optionally aliphatic and/or cycloaliphatic monoalcohols. The amounts of the reactants are chosen in such a way that branched polyesters having OH-functionalities of ≧2.3 result. Polyols having at least three OH-groups are used in an amount corresponding to more than 0.3 equivalents of OH-groups per one equivalent of carboxyl groups. The carboxyl groups may be derived up to 45 % from monocarboxylic acids. The excess of total OH is at least 1.20 equivalents OH per one equivalent of carboxyl groups.

Compounds bearing hydroxyl and carboxyl groups simultaneously can also be used for the production of the polyester resins used according to the invention, so far as these compounds are free from aromatic structural units. Examples of them are dihydroxymonocarboxylic acids, as e.g. dimethylolpropionic acid.

Examples of (cyclo)aliphatic, optionally unsaturated, mono- and dicarboxylic acids are sebacic acid, decanedicarboxylic acid, dodecanedicarboxylic acid, adipic acid, azelaic acid, maleic acid, succinic acid, fumaric acid, tetrahydrophthalic acid, 1,4-cyclohexanedicarboxylic acid, 1,3-cyclohexanedicarboxylic acid, hexahydrophthalic acid, methylhexahydrophthalic acid, dimeric fatty acids, monocarboxylic acids with a carbon number of 6 to 24, and maleic, hexahydrophthalic and succinic anhydrides.

Examples of (cyclo)aliphatic mono- and polyalcohols are hydrogenated bisphenol A, ethylene glycol, diethylene glycol, 1,3-propanediol, 1,2-propanediol, 2-methyl-1,3-propanediol, dipropylene glycol, glycerol, pentaerythritol, neopentyl glycol, trimethylolpropane, trimethylolethane, butanediol, pentanediol, hexanediol, decanediol, hydroxypivalic acid neopentylglycol ester and monoalcohols with a carbon number of 6 to 24.

The production processes for such polyester resins are known to the expert and described for example in Houben-Weyl "Methoden der Organischen Chemie" Makromolekulare Stoffe II, Vol. 14/2, pages 1–42, Georg Thieme Verlag, 1962, and in Ullmann, "Encyclopädie der technischen Chemie" 4th Edition, Vol. 19, pages 61–88.

The polyester resins used according to the invention are preferably produced according to the melt process known to the expert at reaction temperatures of about 150° to 250° C.

The polyester resins used for the production of coating agents according to the invention, suitable in particular as clear coats, are used in proportions of 45–85 wt %, preferably of 55–70 wt %, relative to the finished lacquer. They can also be used as mixtures of several different polyester resins, provided they only conform to the aforementioned definitions.

Aminoplastic resins (IIa) and/or blocked isocyanates (IIb) are used as cross-linker component (II). These are partially or completely etherified amine-formaldehyde condensation resins and/or blocked polyisocyanates with at least two reactive positions per molecule.

Examples of compounds (IIa) are indicated in the following: amine-formaldehyde condensation resins that are formed for example by reaction of aldehydes with melamine. In this connection the aldehydes can be monofunctional but also polyfunctional. Examples of these are formaldehyde and its polymerization products, such as paraformaldehyde, polyoxymethylene, trioxane or aliphatic and cyclic aldehydes, such as glyoxal, acetaldehyde, acrolein, propionaldehyde, butyraldehyde and furfural. According to reaction conditions (pH, temperature) and degree of methylolation, resins with different molecular weights and different reactivity are obtained. The condensation with formaldehyde, furfural, paraformaldehyde, polyoxymethylene or trioxane is generally carried out with the addition of weak acids or bases as catalyst. Strong acids are used for example in the case of condensation with acrolein, glyoxal, acetaldehyde, propionaldehyde or butyraldehyde. In this case the primary reaction product is neutralized, then aldehyde added and reaction continued with addition of weak acids or bases. The preferred aldehyde is formaldehyde. The alcohol groups, preferably methylol groups, of the aldehyde condensation products are partially or preferably completely etherified with alcohols.

Those amine-formaldehyde resins are preferred of which the principal amount of the methylol groups is reacted with monoalcohols or their mixtures. Methanol, ethanol, propanol, butanol, heptanol, benzyl alcohol and other aromatic alcohols, cyclic alcohols as well as ethoxyethanol or butoxyethanol are particularly preferred. If it is intended to incorporate alcohols with more than 4 C atoms, the methylol group is first etherified with a lower alcohol and the higher alcohol then introduced by transetherification. The preferred alcohols are low aliphatic monoalcohols, such as methanol and/or butanol and its isomers. Melamine resins that are reacted with 3 to 6 moles of formaldehyde and subsequently completely etherified with methanol are particularly preferred. The resins are produced according to the prior art and are offered by many firms as sales products. Unsaturated melamine types are formed by etherification with hydroxyalkyl (meth)acrylates or allyl alcohol. Usual carbamyl-methylated melamine resins that are produced by reaction of alkoxymethylated melamine resins with alkyl carbamates under weakly acidic conditions can also be used. Such condensates of type (IIa) are described for example in Ullmann "Encyclopedia of Industrial Chemistry", 5th Edition, Vol A2, Chapter "Aminoresins" pages 115–141 (1985) and Houben-Weyl, "Methoden der Organischen Chemie", Vol. 14/2, pages 319–388 (1962).

A group of examples of cross-linking agents of type (IIb) is represented by the class of the capped or blocked polyisocyanates that include diisocyanates. As capped isocyanates, any desired di- and/or polyisocyanates can be used in which the isocyanate groups have been reacted with a compound that contains active hydrogen. The capped di- and/or polyisocyanates react at elevated temperature, generally between about 90° to 220° C. with the film formers Blocked di- and/or polyisocyanates are produced e.g. by reacting a multifunctional isocyanate with at least a stoichiometric amount of amonofunctional compound containing active hydrogen (Zerewitinoff reaction), suitably at temperatures of 50° to 80° C., wherein usual catalysts, such as basic catalysts, like tertiary amines and/or small amounts of tin salts, like dibutyltin dilaurate, can optionally be added. Appropriate prepolymers containing isocyanate groups also can be used as di- and/or polyisocyanates. The organic di-and/or polyisocyanates have a molecular weight of 112 to 2000, preferably 140 to 1000, and suitably a mean isocyanate functionality of 2 to 8. Suitable polyisocyanates are for example compounds of the idealized formula $$E(N{=}C{=}O)_s$$

in which E represents an aliphatic hydrocarbon radical with 2 to 18, preferably 6 to 10, carbon atoms or a cyclic hydrocarbon radical with 6 to 15 carbon atoms, and s a number of 2 to 5, preferably 2 to 3.

Typical examples of such polyisocyanates are propylene diisocyanate, ethylethylene diisocyanate, dimethylethylene diisocyanate, trimethylene diisocyanate, pentamethylene diiscocyanate, hexamethylene diisocyanate, trimethylhexane diisocyanate, 1,12-dodecane diisocyanate, 1,18-octadecane diisocyanate, cyclopentane diisocyanate, cyclohexane-1,3-and -1,4-diisocyanate as well as any mixtures of these isomers, methylcyclohexane diisocyanate, 1-isocyanato-3,3,5-trimethyl-5-isocyanatomethylcyclohexane, perhydro-2,4'- and/or -4,4'-diphenylmethane diisocyanate. Diisocyanates produced on a large scale such as hexane diisocyanate, isophorone diisocyanate or dicyclohexane diisocyanate are particularly preferred. Apart from the low-molecular polyisocyanates mentioned by way of example, the higher-molecular isocyanate polymers known in polyurethane chemistry and based on polyisocyanates free from urethane groups and higher-molecular polyhydroxy compounds can also be used as a polyisocyanate component. Suitably in this case (n+1) moles of the above described diisocyanates are reacted with n moles of a difunctional compound reactive towards isocyanate at temperatures of suitably 50° to 120° C. in the melt or in presence of inert solvents, that can be either low-molecular or high-molecular, with a molecular weight of 62 to 1000. If an excess of diisocyanate is used, the excess of diisocyanate must be distilled off again. Low-molecular dialcohols means suitably the various isomers of linear, branched and cyclic carbon compounds with 2 to 20 carbon atoms and two secondary and/or primary hydroxyl groups. Typical examples of these are 1,4-butanediol, 1,6-hexanediol, trimethylhexanediol, bis(hydroxymethyl)cyclohexane, neopentyl glycol, hydroxypivalic acid neopentylglycol ester and N-methyldiethanolamine. Suitable higher-molecular polyhydroxy compounds are also the polyesterdiols, polycaprolactonediols, polycaprolactamdiols, polycarbonatediols, polyurethanediols and polyglycoletherdiols, all known from polyurethane chemistry. Long-chain primary and secondary diamines can also be used, such as 1,6-hexanediamine, and adducts of 2 moles glycidyl ethers or glycidyl esters to hexane diamine, N,N'-cyanethylethylenediamine or bis-N,N'-cyanethylpolyoxypropylenediamine.

The so-called "lacquer polyisocyanates" that are produced from known diisocyanates are particularly suitable as polyisocyanates. Thus tris(6-isocyanatohexyl)biuret is formed from hexane diisocyanate and water. By trimerization of hexane diisocyanate tris(6-isocyanatohexyl)isocyanurate is obtained, optionally mixed with its higher homologues as well as further polyisocyanates having isocyanurate groups built up from isophorone diisocyanate. Polyisocyanates having urethane groups that can be obtained for example by reaction of excess quantities of diisocyanate with simple polyhydric alcohols of molecular weight 62 to 300, particularly trimethylolpropane, and optionally destructive removal of the unreacted excess diisocyanate, are very good isocyanates to use. Thus for example blocked triisocyanates or blocked higher-molecular reaction products of triisocyanates with dialcohols are particularly preferred. Suitably in this reaction, the following molecular ratios are maintained: triisocyanate: diol: protecting group is as y: (y−1) : (y+2), wherein y=1 to 6, preferably 2 to 3. Agents that block the isocyanates contain only a single amine, amide, imide, lactam, thio or hydroxyl group. Volatile compounds containing active hydrogen and with low molecular weights, preferably of not more than 300, more preferably of not more than 200, are generally used.

Thus the following compounds for example have proved their worth: aliphatic or cycloaliphatic alcohols, such as n-butanol, 2-ethylhexanol, cyclohexanol, phenols, tertbutylphenols, dialkylaminoalcohols such as dimethylaminoethanol, oximes such as methyl ethyl ketoxime, lactams such as caprolactam or 2-pyrrolidone, imides such as phthalimide or N-hydroxymaleimide, hydroxalkyl esters, malonic acid or ethyl acetoacetate.

β-hydroxyglycols or -glycol ethers and glycolamides are also recommended, however. Oximes and lactams are of particular interest as capping agents, since the polyisocyanates capped therewith react at relatively low temperature. Also, more than one kind of protecting group, preferably such with different reactivity, can be used for blocking. Thus it is possible for example to use a mixture of two or more differently blocked polyisocyanates or one polyisocyanate that is blocked with two or more different protecting groups.

The cross-linker components (II) that are used according to the invention for the production of the coating agents are preferably free from aromatic structural units and are used in proportions of 10 to 40, preferably below 30 wt %, relative to the finished coating agent. The compounds of type (II) can be used alone or in a mixture.

The coating agent according to the invention can furthermore contain liquid, low-molecular, hydroxy-functional reactive diluents, i.e. compounds that become chemically incorporated in the lacquer film during the stoving process, with at least 2 hydroxyl groups per molecule and OH numbers in the range of 400 to 800 mg KOH/g. For example, polyols, such as polyether polyols, polyester polyols, polycarbonate polyols and polyurethane polyols with molecular weights of for example 150 to 1000, are suitable. For example, commercial products such as polycaprolactone polyols obtainable by reaction of polyols with caprolactone, polyether polyols, such as e.g. triethylene glycol, obtainable by reaction of oxirane compounds with polyols and/or water, or polyurethane polyols obtainable by reaction of polyamines with cyclic carbonates, are suitable.

The reactive diluents are used in proportions of 0 to 20 wt %, relative to the finished coating agent. The upper limit is, preferably below 15 wt % and the lower limit is preferably 5, particularly preferably 10 wt %. The reactive diluents can be used alone or in a mixture.

The coating agent according to the invention can contain solvents in proportions up to 10, preferably below 5, particularly preferably below 3 wt %, relative to the finished coating agent. In this connection, solvents means solvents usual in the lacquer industry, in particular those whose boiling point or range does not fall below 170° C. They are inert in the lacquer system, i.e. they are not chemically bound into the lacquer film during the stoving process. Examples are paraffins, e.g. of $C_{11}$–$C_{13}$; aromatics, individually or in a mixture, with e.g. $C_{12}$–$C_{14}$; or esters, e.g. 2,2,4-trimethyl-1,3-pentanediol monoisobutyrate.

The coating agent according to the invention can optionally contain small amounts of cross-linking catalyst. These are commercial acid catalysts, as for example organic sulphonic acids, such as p-toluenesulphonic acid, dodecylbenzenesulphonic acid and dinonylnapththalenesulphonic acid. The acid catalysts are used in blocked form. Examples are salts of the sulphonic acids with amines, such as diisopropylamine, morpholine, pyridine and 2-amino-2-methyl-1-propanol. The use of sulphonic acids blocked with epoxide compounds, as e.g. p-toluenesulphonic acid blocked with versatic acid glycidyl ester, is particularly preferred. They are used in the usual amounts.

The coating agents according to the invention for clear coating agents can furthermore contain customary lacquer-technology additives, as for example light protection agents, levelling agents, plasticizers, transparent pigments and fillers, spreading agents, antifoams, and agents with influence on the viscosity or rheology (e.g. substituted polyureas). The coating agents according to the invention are produced by simple mixing of components (I) and (II) as well as optionally subsequent addition of reactive diluents, solvents, catalysts and additives. In the course of this, additives existing in solid form can be dissolved in the liquid components present or they are brought to a suitable particle size by grinding by known processes.

The work is preferably performed by admixing component (II) with component (I) at elevated temperature. The temperature is at the same time so chosen that reaction between components (I) and (II) is certainly avoided. The temperatures are below 100° C., preferably below 80° C.

The coating agents according to the invention are one-component systems. They are distinguished by a high stability on storage and can be stored for more than six months without substantial change of viscosity. Suitable substrates are metallic substrates, plastics or substrates precoated with coatings.

The coating agents are applied by paint roller, by rolling or by spraying, preferably by means of spray application processes. Examples of these are compressed air spraying, airless spraying or electrostatic spraying. A particular embodiment of these processes is hot spraying techniques, that can be applied with the optional support of supercritical solvents.

Hot spraying techniques are preferably used, such as e.g. hot air hot-spraying. For this a temperature range of 40°–90° C., preferably of 60°–80° C., is chosen. The temperature is so chosen that good spraying and good levelling are guaranteed. Furthermore the coating agent should undergo no chemical changes even in the case of repeated spraying, in order to make recycling possible. The thermal stress of the coating agent can also be kept small by measures at the application device. Thus for example the heating to application temperature can first occur in the spray gun. Furthermore gentle heating techniques, e.g. by hot air, can be applied. By these means, recyclability can be assured. At the same time a proportion of optionally worked-up overspray is added to fresh coating agent.

The coating agents according to the invention, especially as clear coating agents for the hot spraying process, have viscosities of 100–400 mPa.s, preferably of 120–200 mPa.s, measured by rotational viscometry at 70° C. and a shear rate of 235 s$^{-1}$. The number-average molecular weight ($M_n$) of the preferred binders for this is 500 to 1500. At the same time the polydispersity is preferably less than 3.0.

Another preferred process is spray application with use of supercritical liquids according to EP-A-0 321 607. In the course of this, a component having a viscosity-reducing effect in the supercritical state is injected into the coating agent before its application, as a result of which the mixture is converted to the supercritical state, so that as a result a suitable viscosity for application can be adjusted. A preferred example of such a component is carbon dioxide. The injection and spraying is optionally supported by elevated temperatures. At the same time the temperature must be set above the critical temperature and the pressure above the critical pressure. In the case of carbon dioxide, the work is carried out for example at 35° to 70° C. and preferably at 40° to 60° C. The pressure is preferably 90 to 140 bar. The spraying process used is for example an airless spray application.

The upper limit of carbon dioxide is determined by the solubility limit of the system: phase separation must not occur. This depends on the pressure and temperature conditions chosen. The amount of carbon dioxide used, relative to the total lacquer mixture, is preferably 10 to 50 wt %.

The viscosity of the pure undiluted coating agent for this special application process is 100 to 1000 mPa.s, measured by rotational viscometry at 70° C. and a shear rate of 235 s$^{-1}$. The number-average molecular weight of component I is preferably 1000 to 2000.

The supercritical component (e.g. the carbon dioxide) escapes during the application and the direct recycling of the overspray is possible, since no enrichment of the supercritical component in the coating agent occurs. In the case of the coating agents according to the invention, recycling means that, after collection of the overspray, they can optionally be worked up again by chemical and physical processes. It is likewise possible as a preferred embodiment for the collected lacquer material, optionally after filtration and addition of missing components, to be reused directly.

The procedure during application is to apply the covering of clear coat made of the coating agent according to the invention to the substrate, e.g. workpieces of metal or plastic such as automobile bodies or parts thereof, which is already provided with other coats of lacquer. During this, the substrate can optionally have an elevated temperature of up to 50° C. This can be achieved by usual process measures, as e.g. hot air, infra-red radiators or oven heating, or the substrate has still higher temperatures from preceding coating processes. A better lacquer surface can thereby be achieved.

After an optionally interposed rest phase, that serves for levelling, the applied coating agent is cross-linked by heating. During this, to achieve a uniform surface, the substrate can be rotated about longitudinal or transverse axes as described e.g. in EP-A-0 278 482.

The stoving temperature is 130° to 170° C., preferably 140° to 160° C. The film thickness of the stoved film is about 20–60 μm, preferably 35–50 μm. In the course of this a cross-linked, hard, glossy lacquer covering is formed. A preferred embodiment is the application of the coating agent according to the invention as a clear coat covering over a base coat, preferably an aqueous base coat. During this the process is operated wet-on-wet, or the base coat is previously dried by heating. A particularly good adhesion of the two layers is then obtained.

With the coating agents formulated according to the invention as clear coat, base coats can for example be overcoated that contain usual base coat or finish pigments; they preferably contain effect pigments, such as e.g. metallic pigments or iriodin pigments. Preferably, polyester, polyurethane or acrylate resins are used as binder base of the base coat. These binders can optionally be cross-linked via cross-linkers (individually or as a mixture), e.g. melamine or isocyanate derivatives. Examples of base coats that can be overcoated with the clear coat according to the invention can be found in DE 36 28 124, DE 37 15 254, DE 37 22 005, DE 39 13 001 and DE 40 11 633.

The coating agents according to the invention are particularly suitable for clear coats that can preferably be used in the motor vehicle sector but also in other areas. The use of the coating agent according to the invention in multicoat lacquer finishes is particularly suitable for automobile series lacquering, but can also be used for other purposes, e.g. for household appliances or in the furniture industry.

In the production of multicoat lacquering, clear coating agents from the coating agents according to the invention produce only small solvent emissions. The overspray is suitable for direct recycling.

EXAMPLE 1

In a reactor suitable for the polyester synthesis, 287 g neopentyl glycol, 57 g ethylene glycol, 134 g trimethylolpropane, 197 g adipic acid, 324 g hexahydrophthalic anhydride and 1 g hypophosphorous acid were slowly melted and intimately mixed. After reaching 170° C., polycondensation with elimination of water started, the temperature being slowly raised to a maximum of 250° C., so that water continually distilled off without the column head temperature exceeding 100° C. After an acid number of 16 mg KOH/g was reached, the mixture was rapidly cooled.

A polyester with an OH number of 229 mg KOH/g and a number-average molecular weight of 800 (gel permeation chromatographic, calibrated with polystyrene standard) was obtained. The polydispersity was 2.5.

To 751.5 g of the polyester obtained, after cooling to 70° C., were added 225.5 g hexamethoxymethylmelamine (degree of polymerization: 1.5). The product was well mixed, and after cooling to 60° C., mixed with 23 g Texanol solvent. 79.42 parts of the aforementioned resin mixture were mixed with stirring successively with 5.83 parts triethylene glycol, 5.83 parts of a commercial polycaprolactone triol with a number-average molecular weight of 300, 2.91 parts of the diester from phthalic acid and 2-ethylhexanol, 1.75 parts versatic acid glycidyl ester-blocked p-toluenesulphonic acid, 1.46 parts of a mixture of commercial levelling agents based on polysiloxane, 0.78 parts of a commercial non-acid-binding HALS-based light protection agent, 1.55 parts of a commercial benzotriazole-based light protection agent and 0.47 parts of a commercial spreading agent based on a low-molecular acrylate resin.

A clear coating agent was obtained, with a viscosity of 160 mPa.s, measured in the rotation viscometer at 70° C. and a shear rate of 235 s$^{-1}$.

EXAMPLE 2

Analogously to Example 1, 368 g neopentyl glycol, 129 g trimethylolpropane, 189 g adipic acid, 312 g hexahydrophthalic anhydride and 1 g hypophosphorous acid were polycondensed until an acid number of 13.5 g KOH/g was reached.

The polyester obtained had an OH number of 200 mg KOH/g and a number-average molecular weight of 800 (gel permeation chromatographic, calibrated with polystyrene standard) at a polydispersity of 2.4.

752.1g of the polyester were mixed with 225 g hexamethoxymethylmelamine (degree of polymerization: 1.5) and 22.9 g Texanol solvent, at 70° C.

82.61 parts of this resin mixture were intimately mixed with 5.65 parts triethylene glycol, 6 parts of the polycaprolactone triol mentioned in Example 1, 1.76 parts of the blocked sulphonic acid according to Example 1, 2.42 parts of a mixture of commercial polysiloxane-based levelling agents and 0.78 parts of each of the light protection agents mentioned in Example 1. A clear coating agent was obtained, with a viscosity of 175 mPa.s, measured in the rotation viscometer at 70° C. and a shear rate of 235 s$^{-1}$.

EXAMPLE 3

Analogously to Example 1, 199 g neopentyl glycol, 119 g ethylene glycol, 139 g trimethylolpropane, 205 g adipic acid, 337 g hexahydrophthalic anhydride and 1 g hypophosphorous acid were polycondensed until an acid number of 16 mg KOH/g was reached.

The polyester obtained had an OH number of 206 mg KOH/g and a number-average molecular weight of 800 (gel permeation chromatographic, polystyrene standard) at a polydispersity of 2.4.

752.1g of the polyester were mixed with 225 g hexamethoxymethylmelamine (degree of polymerization: 1.5) and 22.9 g Texanol solvent, at 70° C.

81 parts of this mixture were intimately mixed with stirring with 6 parts of triethylene glycol, 6 parts of the polycaprolatone triol mentioned in Example 1, 1.7 parts of the blocked sulphonic acid mentioned in Example 1, 3 parts of a mixture of commercial polysiloxane-based levelling agents, 1 part of each of the light protection agents mentioned in Example 1 and 0.3 parts of the spreading agent mentioned in Example 1.

A clear coating agent was obtained, with a viscosity of 146 mPa.s, measured in the rotation viscometer at 70° C. and a shear rate of 235 s$^{-1}$.

The clear coating agents mentioned in Examples 1 to 3 were examined as follows:

Autobody sheets precoated with the commercial cataphoretic coating (18 μm) used in automotive coating and with commercial crack filler (35 μm) were lacquered with commercial water-dilutable metallic base coat in a dry film thickness of 15 μm and predried for 6 min at 80° C. Directly afterwards the clear coatings mentioned in Examples 1 to 3 were applied wet-on-wet by hot spraying at 70° C. and stoved for 30 min at 150° C. object temperature.

In all cases a hard, glossy, multilayer lacquer with good adhesion and good optical quality was obtained. The crosslinking of the clear coat was tested with a swab soaked in methyl ethyl ketone. After 100 double strokes the clear coat surface was unaffected.

EXAMPLE 4

Example 3 was repeated, with the difference that carbon dioxide was injected into the clear coating agent in the ratio 100:45 (31 wt % $CO_2$ relative to the whole composition) and the coating agent applied at 55° C. and 125 bar by the airless spraying process. After 5 min flashing off the finish was stoved for 30 min at 150° C. A similar resulting lacquer to that from Example 3 was obtained.

EXAMPLE 5

Analogously to Example 1, 431.1 g pentaerythritol, 450.8 g hexahydrophthalic anhydride, 616.6 g isononanoic acid and 1.5 g hypophosphorous acid Werepolycondensed until an acid number of 18 mg KOH/g was reached.

The polyester obtained had an OH number of 137 mg KOH/g and a number-average molecular weight of 1900 (gel permeation chromatographic, polystyrene standard) at a polydispersity 3.2.

750g of the polyester were mixed with 227 g hexamethoxymethylmelamine (degree of polymerization: 1.5) and 23 g Shellsol R (aromatic hydrocarbon), at 70° C. 77.6 parts of this resin mixture were mixed with 7 parts triethylene glycol, 6.5 parts of the polycaprolactone triol described in Example 1, 1.5 parts of the phthalic acid diester mentioned in Example 1, 1.8 parts of the blocked sulphonic acid according to Example 1, 3 parts of the mixture of commercial levelling agents according to Example 1, 0.5 parts of the HALS light-protection agent according to Example 1, 1.6 parts of the benzotriazol light protection agent according to Example 1 and 0.5 parts of the spreading agent according to Example 1.

A clear coating agent was obtained, with a viscosity of 490 mPa.s, measured in the rotation viscometer at 70° C. and a shear rate of 235 s$^{-1}$.

The clear coating agent was applied analogously to Example 4 with a similar resultant lacquer, with the difference that clear coating agent and carbon dioxide were used in the ratio 100:72 (42 wt % $CO_2$, relative to the whole composition) and were applied at 60° C. and 125 bar.

In each of the examples 1, 2 and 3 1.07 equvalents of diol and 0.43 equivalents of triol were reacted with one equivalent dicarboxylic acid.

In example 5 1.3 equivalents of tetrol were reacted with 0.4 equivalents of monocarboxylic acid and with 0.6 equivalents of dicarboxylic acid.

We claim:

1. A process for the production of a multicoat lacquer finish, comprising:

preparing a clear coating agent by a process consisting essentially of:

reacting together 45–85% of one or more polyester resins having a branched structure and being essentially free from acetal-functional groups and from aromatic structural units, and which have a number average molecular weight of 350–3000 and a polydispersity of less than 3.5, and 10–40 wt % of one or more cross-linking agents based on at least one member selected from the group consisting of aminoplastic resins, blocked di-isocyanates and blocked polyisocyanates, 0–20 wt % of one or more reactive diluents, and 0–10 wt % of one or more organic solvents having a boiling point or boiling range not less than about 170° C.;

thereby forming a clear coating agent which has a viscosity of 100–1000 mPa.s, measured by rotation viscometry at 70° C. and a shear rate of 235 s$^{-1}$;

hot spraying the clear coating agent on a base coat layer and stoving to produce a lacquer finish, thereby chemically incorporating the reactive diluent, if present, into the lacquer finish.

2. A process according to claim 1, characterized in that the process is operated at a spraying temperature of 40° to 90° C.

3. A process according to claim 1, characterized in that before the application of the clear coat, a supercritical solvent is injected.

4. A process according to claim 3, characterized in that supercritical $CO_2$ is injected.

5. A process according to claim 1, characterized in that the process is operated at a temperature of 60° to 80° C.

6. A process according to claim 3, characterized in that the process is operated at a temperature of 35° to 70° C.

7. A process according to claim 1, characterized in that before the coating process the substrate has an elevated temperature.

8. A process according to claim 1, characterized in that the base coat layer has been produced from an aqueous coating agent.

9. A process according to claim 1, characterized in that the wet-on-wet method is used.

10. A substrate coated with a multicoat lacquer finish obtained by the process of claim 1.

11. A process according to claim 1 in which the hot spraying step is carried out in the absence of a super critical fluid.

* * * * *